United States Patent
Choi et al.

(10) Patent No.: US 10,518,250 B2
(45) Date of Patent: Dec. 31, 2019

(54) FERRITE-BASED CATALYST COMPOSITE, METHOD OF PREPARING THE SAME, AND METHOD OF PREPARING BUTADIENE USING THE SAME

(71) Applicant: LG CHEM, LTD., Seoul (KR)

(72) Inventors: Dae Heung Choi, Daejeon (KR); Dong Hyun Ko, Daejeon (KR); Kyong Yong Cha, Daejeon (KR); Myung Ji Suh, Daejeon (KR); Ye Seul Hwang, Daejeon (KR); Sun Hwan Hwang, Daejeon (KR); Seong Min Kim, Daejeon (KR); Jun Han Kang, Daejeon (KR); Joo Hyuck Lee, Daejeon (KR); Hyun Seok Nam, Daejeon (KR); Sang Jin Han, Daejeon (KR); Jun Kyu Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 71 days.

(21) Appl. No.: 15/746,758

(22) PCT Filed: Feb. 17, 2017

(86) PCT No.: PCT/KR2017/001747
§ 371 (c)(1),
(2) Date: Jan. 22, 2018

(87) PCT Pub. No.: WO2017/150830
PCT Pub. Date: Sep. 8, 2017

(65) Prior Publication Data
US 2018/0214854 A1    Aug. 2, 2018

(30) Foreign Application Priority Data
Mar. 4, 2016    (KR) .................. 10-2016-0026563

(51) Int. Cl.
*B01J 23/745*    (2006.01)
*B01J 23/75*    (2006.01)
(Continued)

(52) U.S. Cl.
CPC ............. *B01J 23/745* (2013.01); *B01J 23/75* (2013.01); *B01J 23/78* (2013.01); *B01J 23/80* (2013.01);
(Continued)

(58) Field of Classification Search
CPC . B01J 23/745; B01J 23/75; B01J 23/78; B01J 23/80; B01J 23/8892; B01J 35/023; B01J 35/08
See application file for complete search history.

(56) References Cited

U.S. PATENT DOCUMENTS 3,998,760 A * 12/1976 Christmann ............. B01J 23/80
502/324
4,083,884 A    4/1978 Purdy
(Continued)

FOREIGN PATENT DOCUMENTS

CN    103055871    4/2013
GB    1251824    11/1971
(Continued)

*Primary Examiner* — Cam N. Nguyen
(74) *Attorney, Agent, or Firm* — Dentons US LLP (57) ABSTRACT

The present invention relates to a ferrite-based catalyst composite, a method of preparing the same, and a method of preparing butadiene using the same. More particularly, the present invention provides a ferrite-based catalyst composite having a shape that allows effective dispersion of excess heat generated in a butadiene production process and prevention of catalyst damage and side reaction occurrence by reducing direct exposure of a catalyst to heat, a method of preparing the ferrite-based catalyst composite, and a method of preparing butadiene capable of lowering the temperature of a hot spot and reducing generation of Cox by allowing active (Continued)

Black Dot → Ferrite Granule sites of a catalyst to have a broad temperature gradient (profile) during oxidative dehydrogenation using the ferrite-based catalyst composite, and thus, providing improved process efficiency.

6 Claims, 3 Drawing Sheets

(51) Int. Cl.
  *B01J 23/78*   (2006.01)
  *B01J 23/80*   (2006.01)
  *B01J 23/889*  (2006.01)
  *B01J 35/02*   (2006.01)
  *B01J 35/08*   (2006.01)
  *B01J 37/00*   (2006.01)
  *B01J 37/03*   (2006.01)
  *B01J 37/08*   (2006.01)

(52) U.S. Cl.
  CPC ......... *B01J 23/8892* (2013.01); *B01J 35/023* (2013.01); *B01J 35/08* (2013.01); *B01J 37/0018* (2013.01); *B01J 37/0072* (2013.01); *B01J 37/033* (2013.01); *B01J 37/082* (2013.01)

(56) References Cited

U.S. PATENT DOCUMENTS

| | | | |
|---|---|---|---|
| 4,332,972 A * | 6/1982 | Christmann | B01J 23/80 585/442 |
| 5,244,641 A | 9/1993 | Khare | |
| 9,448,500 B2 * | 9/2016 | Harada | G03G 9/0839 |
| 9,550,174 B2 | 1/2017 | Kwon et al. | |
| 9,907,816 B2 * | 3/2018 | Pennell | A61K 9/1611 |
| 2010/0081855 A1 * | 4/2010 | Pelati | B01J 23/78 585/444 |
| 2014/0141965 A1 | 5/2014 | Xiong et al. | |

FOREIGN PATENT DOCUMENTS

| | | |
|---|---|---|
| JP | 2013536066 | 9/2013 |
| KR | 10-2012-0009687 | 2/2012 |
| KR | 10-2013-0045913 | 5/2013 |
| KR | 10-2014-0082869 | 7/2014 |
| KR | 10-2014-0131870 | 11/2014 |
| WO | 2012011659 | 1/2012 |
| WO | 2012030891 | 3/2012 |

\* cited by examiner

Black Dot → Ferrite Granule

FERRITE-BASED CATALYST COMPOSITE, METHOD OF PREPARING THE SAME, AND METHOD OF PREPARING BUTADIENE USING THE SAME

CROSS-REFERENCE TO RELATED APPLICATION

This application is a National Stage Application of International Application No. PCT/KR2017/001747 filed on Feb. 17, 2017, which claims priority to and the benefit of Korean Patent Application No. 10-2016-0026563, filed on Mar. 4, 2016, in the Korean Intellectual Property Office, all of which are incorporated herein in their entirety by reference for all purposes as if fully set forth herein.

TECHNICAL FIELD

The present invention relates to a ferrite-based catalyst composite, a method of preparing the same, and a method of preparing butadiene using the same. More particularly, the present invention relates to a ferrite-based catalyst composite having a shape that allows effective dispersion of excess heat generated in a butadiene production process and prevention of catalyst damage and side reaction occurrence by reducing direct exposure of a catalyst to heat, a method of preparing the ferrite-based catalyst composite, and a method of preparing butadiene capable of lowering the temperature of a hot spot and reducing generation of Cox by allowing active sites of a catalyst to have a broad temperature gradient (profile) during oxidative dehydrogenation using the ferrite-based catalyst composite, and thus, providing improved process efficiency.

BACKGROUND ART

Butadiene is an intermediate in petrochemical products and demand therefor and value thereof are increasing worldwide. For example, 1,3-butadiene is generally prepared by naphtha cracking, direct butene dehydrogenation, oxidative butene dehydrogenation of generating 1,3-butadiene and water through reaction between butene and oxygen, or the like.

Oxidative butene dehydrogenation is very advantageous in that stable water is generated through this reaction. In addition, since oxidative butene dehydrogenation is an exothermic reaction unlike direct butene dehydrogenation, 1,3-butadiene may be produced in a high yield even at low reaction temperature, compared to direct dehydrogenation. Accordingly, oxidative butene dehydrogenation does not require additional heat supply, thereby being very suitable as a commercial process.

Figure 2:
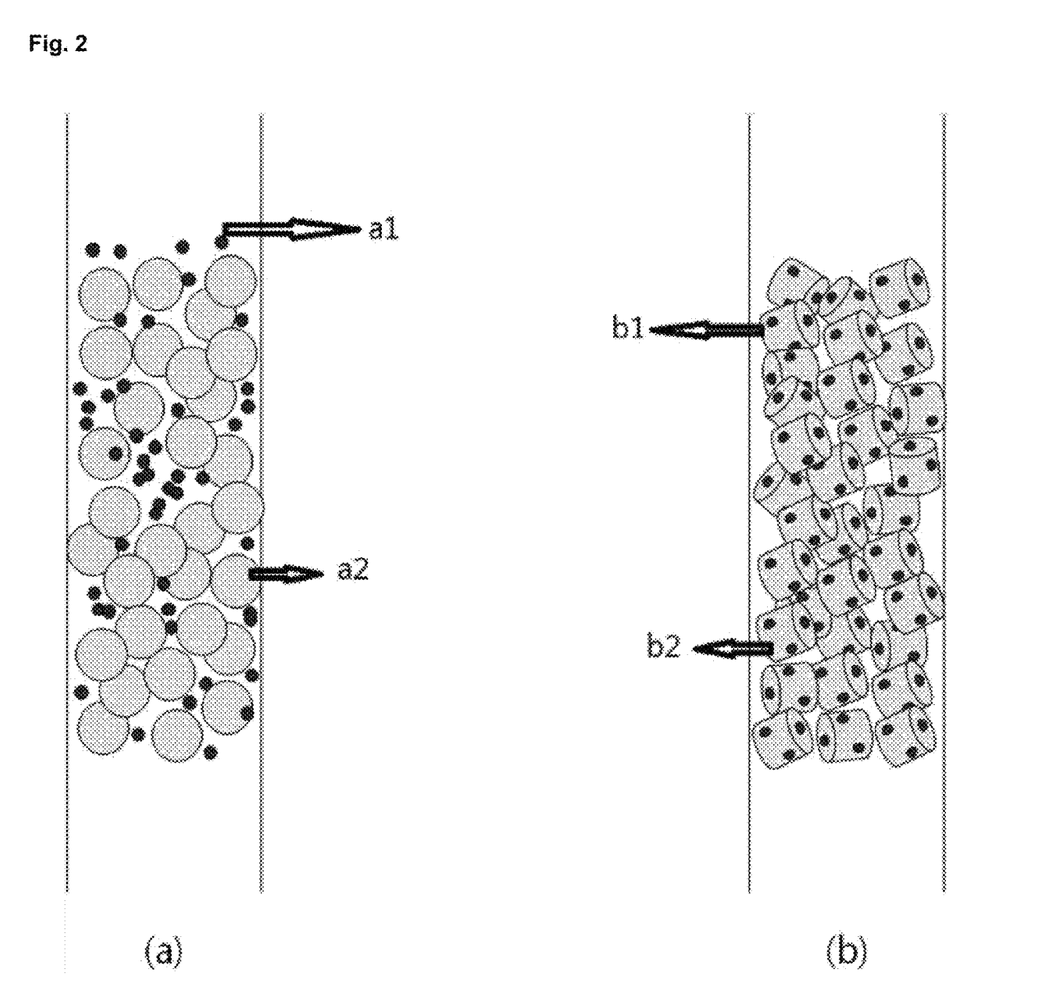
FIG. 2 is a schematic view illustrating reactors for preparing butadiene filled with a ferrite catalyst. Particularly.

However, when heat generation is excessive, reactants are completely oxidized, whereby a side reaction wherein a large amount of Cox is generated may occur. That is, in the case of a ferrite-based catalyst mainly used as a catalyst for oxidative butene dehydrogenation, heat is excessively generated during reaction, thereby causing a relatively high-temperature hot spot. Here, a hot spot refers to a spot or area, the temperature of which is highest due to exothermic reaction, in a fixed bed type catalyst reactor (see graphs of catalysts of FIGS. 2a and 2b illustrated in FIG. 3, a spot at which the temperature inside a reactor elevated by red heat is highest). In particular, excess heat generated at active sites of a catalyst has been known to cause catalyst damage and side reactions. Such catalyst damage and side reactions consequentially cause decrease in butadiene process efficiency.

Referring to FIG. 2a, a catalyst (corresponding to black spots indicated by a1) is physically mixed with an inert material such as aluminum (Al) balls (indicated by a2) to disperse excess heat by diluting the catalyst. However, it can be confirmed from FIG. 2a that it is difficult to accomplish uniform dispersion and, to effectively control a hot spot of a catalyst layer due to direct exposure of a catalyst (a1) to excess heat.

RELATED ART DOCUMENT (Patent Document 1) KR10-2014-0082869A

DISCLOSURE

Technical Problem

Therefore, the present invention has been made in view of the above problems, and it is one object of the present invention to provide a ferrite-based catalyst composite prepared by mixing a ferrite catalyst with an inert binder and uniformly dispersing the same to effectively disperse excess heat generated in a butadiene production process and prevent catalyst damage during reaction and side reaction occurrence, and a method of preparing the ferrite-based catalyst composite.

It is another object of the present invention to provide a method of more efficiently preparing butadiene by effectively dispersing excess heat and allowing active sites of a catalyst to have a broad temperature gradient (profile) to lower the temperature of a hot spot during reaction and reduce generation of COx.

The above and other objects can be accomplished by the present disclosure described below.

Technical Solution

In accordance with one aspect of the present invention, provided is a ferrite-based catalyst composite, including 20 to 99% by weight of inert binder particles and 1 to 80% by weight of ferrite-based catalyst granules dispersed and inserted into the inert binder particles.

In accordance with another aspect of the present invention, provided is a method of preparing a ferrite-based catalyst composite, wherein the ferrite-based catalyst composite is molded by mixing ferrite-based catalyst granules, inert binder particles, and a liquid binder, wherein a weight ratio of the ferrite-based catalyst granules to the inert binder particles is 1:99 to 80:20.

In accordance with yet another aspect of the present invention, provided is a method of preparing butadiene, wherein a reactor is filled with the ferrite-based catalyst composite according to any one of claims 1 to 5, butadiene is prepared from C4 raffinate, and, when a change in hot spot temperature (° C.) at a position before 50 mm in a longitudinal direction of the reactor is Td based on a hot spot inside the reactor in which a layer composed of the catalyst composite is formed, Td≤65.

Advantageous Effects

As apparent from the fore-going, the present invention advantageously provides a ferrite-based catalyst composite having a shape that allows effective dispersion of excess heat generated in a butadiene production process and prevention of catalyst damage and side reaction occurrence by reducing direct exposure of a catalyst to heat, a method of preparing the ferrite-based catalyst composite, and a method of preparing butadiene capable of lowering the temperature of a hot spot and reducing generation of Cox by allowing active sites of a catalyst to have a broad temperature gradient (profile) during oxidative dehydrogenation using the ferrite-based catalyst composite, and thus, providing improved process efficiency.

DESCRIPTION OF DRAWINGS

FIG. 2(a) illustrates a reactor for preparing butadiene in which a ferrite catalyst powder and an inert binder are physically mixed and filled according to a conventional manner (corresponding to non-uniform dispersion), and FIG. 2(b) illustrates a reactor for preparing butadiene filled with a composite that includes ferrite-based catalyst granules dispersed and inserted into inert binder particles according to the present disclosure (corresponding to relatively uniform dispersion).

BEST MODE

Hereinafter, the present invention is described in detail.

The present inventors confirmed that, when a granule-type ferrite-based catalyst is dispersed and inserted into an inert binder, excess heat generated during a butadiene preparation process is effectively dispersed, direct exposure of a catalyst to heat is reduced, and a change in hot spot temperature of a catalyst layer filled in a reactor is effectively controlled. Based on this finding, the present invention has been completed.

Hereinafter, a ferrite-based catalyst composite according to the present invention is described in detail.

The ferrite-based catalyst composite according to the present invention may include, for example, 20 to 99% by weight of inert binder particles and 1 to 80% by weight of ferrite-based catalyst granules dispersed in the inert binder particles. With this shape and within this range, the ferrite catalyst granules are uniformly dispersed in the inert binder particles and direct exposure of the catalyst to heat is reduced, whereby a change in hot spot temperature of a catalyst layer may be controlled.

The inert binder may be an aluminum compound, a silica compound, a silica aluminum compound, or a mixture thereof as a carrier generally used in the art to which the present invention pertains. For example, a silica alumina compound sold as bentonite, or the like may be used.

The inert binder may be included in an amount of 20 to 99% by weight, 20 to 95% by weight, 50 to 90% by weight, or 60 to 90% by weight with respect to the ferrite-based catalyst composite. Within this range, a hot spot may be effectively controlled, compared to the case in which a catalyst and an inert binder are physically mixed in the same ratio (e.g., catalyst illustrated in FIG. 2a).

The ferrite-based catalyst of the composite of the present invention may be a spinel-type metal oxide, a pyramid-type oxide, or a mixture thereof, but the present invention is not limited thereto.

The spinel-type metal oxide may be, for example, an oxide of a trivalent cation iron (Fe) and a divalent cation metal. Here, the divalent cation metal may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co). Preferably, the divalent cation metal is one or more selected from the group consisting of zinc (Zn), magnesium (Mg), manganese (Mn), and cobalt (Co). As a particular example, the spinel-type metal oxide may be a spinel ferrite of a zinc ferrite catalyst ($ZnFe_2O_4$), or a spinel ferrite of a manganese ferrite catalyst ($MnFe_2O_4$).

The pyramid-type oxide may be, for example, an oxide of a trivalent cation iron (Fe). As a particular example, the pyramid-type oxide may be a pyramid-type ferrite ($\alpha$-$Fe_2O_3$).

The ferrite-based catalyst may be prepared by various methods known in the art to which the present invention pertains. In an embodiment, the ferrite-based catalyst may be prepared according to the following methods:

A trivalent cation iron (Fe) precursor and a divalent cation metal precursor are dissolved in distilled water, thereby preparing an aqueous precursor solution.

Subsequently, the aqueous precursor solution and a basic aqueous solution are fed dropwise into a coprecipitation tank containing distilled water. Preferably, pH of a coprecipitation solution is kept constant. The coprecipitation solution is filtered, thereby obtaining a coprecipitate.

The metal precursors are not specifically limited and may be any one generally used in the art to which the present invention pertains.

The divalent metal cations may be derived from, for example, zinc (Zn), magnesium (Mg), manganese (Mn), or cobalt (Co), and the precursor thereof may be, without being specifically limited to, a chloride, a carbonate, a nitrate, an acetate, an oxide, or the like.

The aqueous precursor solution may be prepared, for example, by dissolving 10% by weight to 30% by weight, 10% by weight to 25% by weight, or 15% by weight to 25% by weight of a trivalent cation iron (Fe) precursor and 3% by weight to 10% by weight, 3% by weight to 8% by weight, or 4 to 7% by weight of a divalent cation metal precursor in 60% by weight to 87% by weight, 67% by weight to 87% by weight, or 68% by weight to 81% by weight of distilled water. Within this range, reactivity of oxidative dehydrogenation may be improved while increasing a catalyst production amount per preparation process.

The aqueous precursor solution may also have an acidic pH.

Room-temperature distilled water is contained in the coprecipitation tank. After adjusting pH of the coprecipitation tank to a neutral or basic pH as needed, pH of a resultant solution is adjusted while respectively supplying, preferably feeding dropwise, the aqueous precursor solution and a basic aqueous solution into the coprecipitation tank.

The basic aqueous solution is not specifically limited so long as it is, for example, an aqueous solution of any one basic substance such as sodium hydroxide or ammonia. For example, the basic aqueous solution may be at a concentration of 10 to 35%, 20 to 33%, or 25 to 30%. Within this range, variation in a pH level inside the coprecipitation tank due to dripping of the aqueous precursor solution during catalyst synthesis may be minimized.

The coprecipitation solution may be subjected, for example, to a stirring step; an aging step; or a stirring and aging step. In this case, coprecipitation of the precursors in the coprecipitation solution may be sufficiently accomplished.

The stirring step, the aging step, or a combination thereof may be carried out, for example, for 30 minutes to 3 hours, 30 minutes to 2 hours, or 30 minutes to 1 hour and 30 minutes.

The filtration may be carried out by any one method generally used in the art to which the present invention pertains. The filtration may be, for example, vacuum filtration. As a particular embodiment, the coprecipitation solution may be filtered under a reduced pressure of 100 to 300 mbar, or 160 to 250 mbar. After the filtration, washing may be carried out as needed.

The method of preparing a catalyst for oxidative dehydrogenation may further include, for example, a step of drying; firing; or drying and firing the coprecipitate.

The filtered coprecipitate may be dried, for example, at 60 to 100° C., 70 to 100° C., or 80 to 100° C. for 12 to 20 hours, 14 to 20 hours, or 14 to 18 hours by means of a general dryer.

The filtered coprecipitate may be fired, for example, for 1 to 10 hours, 3 to 8 hours, or 5 to 7 hours at 400 to 800° C., 500 to 800° C., or 550 to 750° C. using a general firing furnace.

An obtained coprecipitate, i.e., a ferrite catalyst, has a granule shape and, in this shape, may form a composite with the inert binder. Here, the expression "dispersed" refers to a state characterized by being dispersed uniformly or non-uniformly in inert binder particles. For example, granules may be randomly distributed in surfaces of inert binder particles and therein. In this case, an effect of reducing direct exposure of a catalyst to heat generated by reaction may be sufficiently provided.

The ferrite-based catalyst granules may have a powder shape having an average particle diameter of 0.1 to 1.25 mm, 0.1 to 0.85 mm, or 0.6 to 0.85 mm. Within this range, direct exposure of a catalyst to heat may be reduced and a change in hot spot temperature may be reproducibly controlled.

The ferrite-based catalyst granules may be included, for example, in an amount of 1 to 80% by weight, 5 to 80% by weight, 10 to 50% by weight, or 10 to 40% by weight with respect to the ferrite-based catalyst composite. Within this range, uniform performance, smooth molding effect, and improved heat generation control effect may be provided.

In an embodiment, the catalyst composite has a spherical shape having a diameter of 1 to 20 mm and a circular or irregular cross section, a cylindrical (prismatic) shape having a diameter of 1 to 20 mm, a circular (square) or irregular cross section, and a height of 1 to 20 mm, or a mixture thereof. Within these diameter and height ranges, uniform dispersion in a reactor may be accomplished, whereby a large amount of heat generated during butadiene preparation may be effectively controlled.

In another embodiment, the catalyst composite has a spherical shape having a diameter of 2 to 15 mm and a circular or irregular circular cross section, a cylindrical (prismatic) shape having a diameter of 2 to 15 mm, a circular (square) or irregular cross section, and a height of 2 to 15 mm, or a mixture thereof.

In still another embodiment, the catalyst composite has a spherical shape having a diameter of 3 to 9 mm and a circular or irregular circular cross section, a cylindrical (prismatic) shape having a diameter of 3 to 9 mm, a circular (square) or irregular cross section, and a height of 3 to 9 mm, or a mixture thereof.

The catalyst composite of the present invention provides uniformly dispersed inert binder and catalyst (see FIG. 2b) instead of physically mixing an inert binder and a catalyst (see FIG. 2a). Due to such uniform dispersion, a surface area capable of acting as active sites of a catalyst composite increases and, as a result, a broad temperature gradient (profile) of the active sites is provided. Accordingly, temperature of a hot spot is lowered, generation of Cox is reduced, and damage to a catalyst and side reactions may be prevented.

The ferrite-based catalyst composite may be prepared, for example, by mixing ferrite-based catalyst granules, an inert binder, and a liquid binder, and molding the same.

Kinds and contents of the ferrite-based catalyst granules and the inert binder are the same as described above.

The liquid binder may be water, methanol, ethanol, propanol, isopropyl alcohol, ethylene glycol, a polyhydric alcohol such as glycerin, or the like. Considering convenience of work, water, isopropyl alcohol, or the like may be used.

A use amount of the liquid binder may be varied. For example, the liquid binder may be used in an amount of 20 to 100 parts by weight, 20 to 80 parts by weight, or 20 to 50 parts by weight based on 100 parts by weight of a sum of the ferrite-based catalyst granules and the inert binder. Within this range, kneading and molding may be properly carried out.

The mixing may be carried out by means of various known mixers, kneaders, etc. The molding may also be carried out by means of various known devices. For example, molding may be carried out in the aforementioned spherical shape, cylindrical shape, prismatic shape, or a mixture thereof using a compression molding machine, an extrusion molding machine, or the like, and a size of a molded product may be varied within the aforementioned range.

After the molding, a molded product may be subjected to, for example, a drying step; a heat treatment step; or a drying and heat treatment step. With regard to these drying and heat treatment steps, the conditions and devices for drying and firing described in the aforementioned ferrite-based catalyst preparation method may be used.

The ferrite-based catalyst composite of the present invention may be used to produce butadiene from C4 raffinate. For example, direct dehydrogenation of butene or oxidative dehydrogenation of butene may be used.

These reactions may be carried out using a tubular reactor, a tank reactor, or a fixed-bed reactor generally used in the art to which the present invention pertains. The fixed-bed reactor may be, for example, a multi-tube reactor or a plate-type reactor.

These reactors may be, for example, a reactor installed in an electric furnace, wherein reaction temperature of a catalyst layer filled in the reactor is kept constant or temperature is kept constant using an oil or a molten salt circulating through the reactor, and oxidative dehydrogenation is performed while reactants continuously pass through the catalyst layer.

Figure 3:
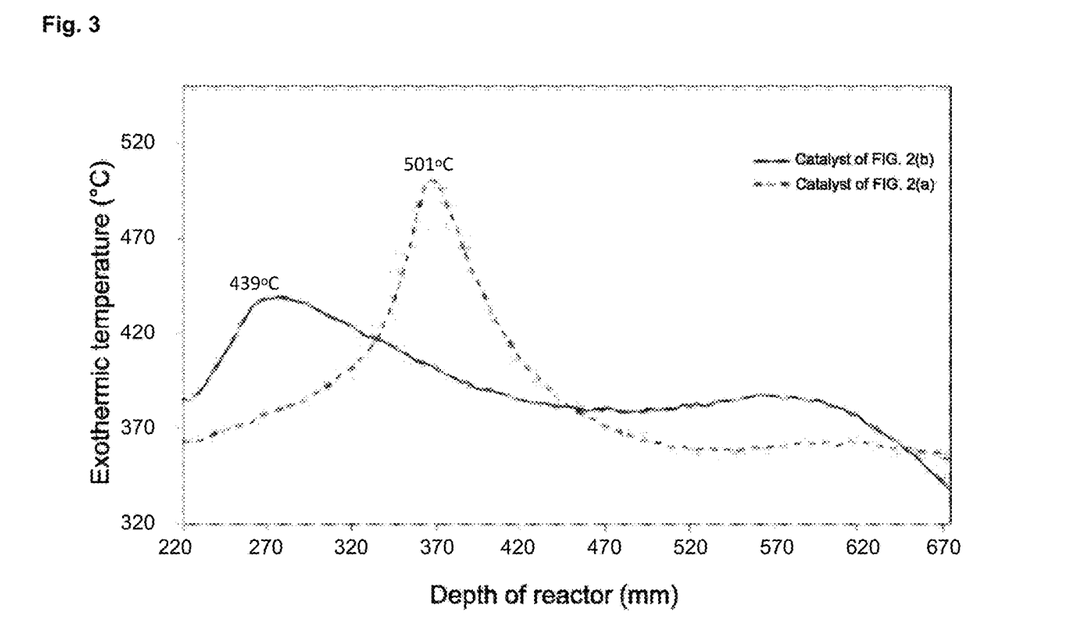
FIG. 3 is a graph illustrating a change in hot spot temperature (° C.) in a longitudinal direction of the reactor, in which a layer composed of the catalyst of each of FIGS. 2(a) and (b) is formed, during generation of butadiene.

In the method of preparing butadiene according to the present invention, a reactor was filled with the ferrite-based catalyst composite, and a change in hot spot temperature (° C.) was measured every 5 mm in a longitudinal direction of the reactor. Results are illustrated in FIG. 3.

When a change in hot spot temperature (° C.) at a position before 50 mm in a longitudinal direction of the reactor is Td based on a hot spot inside the reactor filled with the catalyst composite layer, Td≤65, Td≤55, or Td≤52 is preferred.

In the oxidative dehydrogenation, a gas hourly space velocity (GHSV) based on butene may be 100 to 2000 $h^{-1}$BE (Butene), 250 to 1000 $h^{-1}$BE, or 250 to 500 $h^{-1}$BE. Within this range, high conversion rate and selectivity are exhibited.

In the oxidative dehydrogenation, for example, one or more selected from the group consisting of carbon dioxide and nitrogen may be further included.

[84] When all of butene, oxygen, steam, and nitrogen are included in the oxidative dehydrogenation, a mole ratio (butene to oxygen to steam to nitrogen) therebetween may be, for example, 1:0.5 to 2:1 to 12:2 to 30, 1:0.6 to 1.5:1 to 10:2 to 10, or 1:0.7 to 1.5:1 to 8:2 to 5.

Within this range, superior operation stability and selectivity are provided.

The oxidative dehydrogenation may be carried out, for example, at a reaction temperature of 250 to 450° C., 290 to 400° C., or 290 to 350° C.

When carbon dioxide is additionally added to the reactants, the oxidative dehydrogenation may further include, for example, a step of recycling carbon dioxide discharged after reaction.

The butene may be, for example, 2-butene.

The butene may be, for example, a 2-butene mixture including 60% of trans-2-butene and 40% of cis-2-butene.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

Preparation Example

<Preparation of Ferrite-Based Catalyst>

18.029 g of zinc chloride ($ZnCl_2$) and 71.495 g of ferric chloride ($FeCl_3$) were dissolved in 233.39 g of distilled water, thereby preparing 322.914 g of an aqueous metal precursor solution. Here, a mole ratio of the metal ingredients included in the aqueous metal precursor solution was Fe:Zn=2:1.

Subsequently, aqueous ammonia was added to 233.39 g of room-temperature distilled water in a coprecipitation tank and the pH of the coprecipitation tank was adjusted to pH 8. The coprecipitation tank was equipped with an aqueous metal precursor solution outlet and an aqueous ammonia solution outlet. A room-temperature aqueous ammonia solution (at a concentration of 28% by mass) was supplied to the coprecipitation tank dropwise through the aqueous ammonia solution outlet while feeding the prepared aqueous metal precursor solution thereinto dropwise through the aqueous metal precursor solution outlet, whereby the pH of a coprecipitation solution in the coprecipitation tank was constantly maintained at 8.

After completing the feeding of the aqueous metal precursor solution, the coprecipitation solution was stirred for 1 hour (maintaining pH 8) such that coprecipitation was sufficiently accomplished. After stopping the stirring, a mixture was allowed to stand at room temperature for 1 hour so that all precipitates were sunken and phase-separation was accomplished.

Subsequently, a coprecipitation solution was vacuum-filtered under a pressure of 200 mbar, thereby obtaining a coprecipitate. The obtained coprecipitate was washed and then dried at 90° C. for 16 hours. Subsequently, the dried coprecipitate was put into a firing furnace and heat-treated at 650° C. for 6 hours, thereby preparing a zinc ferrite catalyst.

Example 1

Preparation of Ferrite-Based Catalyst Composite

The zinc ferrite catalyst synthesized in the preparation example was pulverized to granules having an average particle diameter of 0.6 to 0.85 mm by means of a pulverizer. Subsequently, the pulverized zinc ferrite catalyst was mixed with bentonite ($Al_2O_3.4SiO_2.H_2O$), as an inert binder, in a weight ratio of 17:83.

The average particle diameter was measured by means of a Nicomp 370 HPL according to a dynamic laser light scattering method.

30 parts by weight of a mixture of water and isopropyl alcohol (in a weight ratio of 1:1), as a liquid binder, were added to 100 parts by weight of the mixture. Subsequently, a resultant mixture was uniformly kneaded by means of a kneader, and was molded into a cylindrical pellet having a diameter of 6 mm, a circular cross section, and a height of 6 mm by means of an extrusion molding machine.

Figure 1:
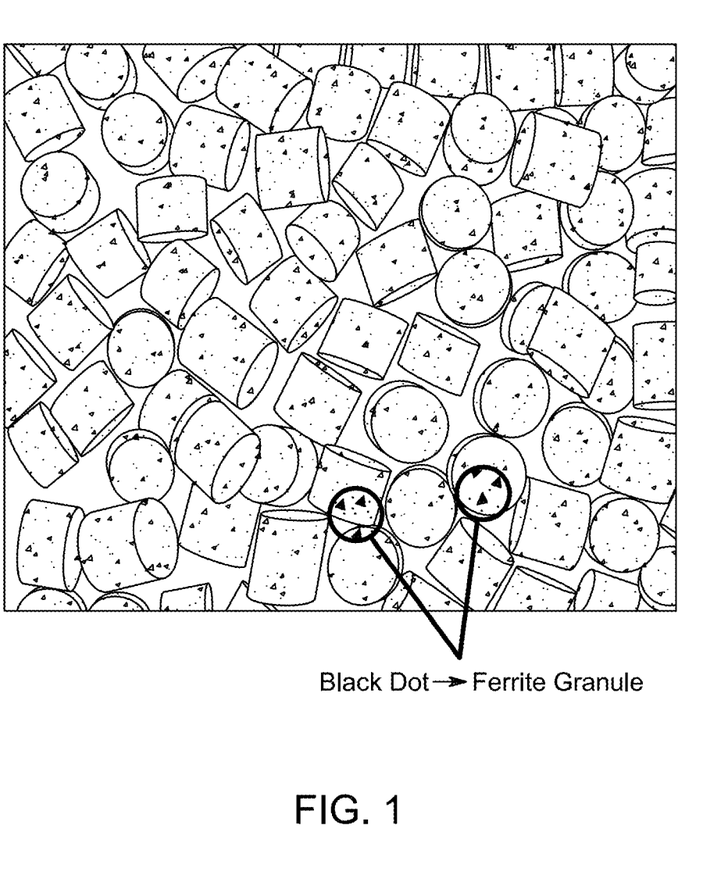
FIG. 1 is a photograph taken by means of a digital camera illustrating that ferrite-based granules (black dots) of a ferrite-based catalyst composite according to the present disclosure are randomly distributed on surfaces of inert binder particles and therein.

The molded pellet was dried at 90° C. for 12 hours and heat-treated at 500° C. for 4 hours, thereby obtaining a catalyst composite. A photograph of the catalyst composite taken with a digital camera is illustrated in FIG. 1. As illustrated in FIG. 1, it was confirmed that ferrite-based catalyst granules were randomly distributed in a black dot shape on surfaces of inert binder particles and therein.

Example 2

A catalyst composite was prepared in the same manner as in Example 1, except that a zinc ferrite catalyst and bentonite were mixed in a weight ratio of 5:95.

Example 3

A catalyst composite was prepared in the same manner as in Example 1, except that a zinc ferrite catalyst and bentonite were mixed in a weight ratio of 3:97.

Comparative Example 1

The zinc ferrite catalyst prepared in the preparation example was pulverized into a powder having an average particle diameter of 0.6 to 0.85 mm by means of a pulverizer.

Comparative Example 2

Physical Dispersion of Ferrite-Based Catalyst and Inert Binder

The zinc ferrite catalyst prepared in the preparation example was pulverized into a powder having an average particle diameter of 0.6 to 0.85 mm by means of a pulverizer, and then shaken and uniformly mixed with aluminum (Al) balls having a diameter of 2 mm in a mix ratio of 4.2:95.8.

[Reaction Test]

Stainless fixed-bed reactors having an inner diameter of 25 mm and a longitudinal length of 700 mm were respectively filled with the catalyst composites (dispersed catalyst product or catalyst) obtained according to Examples 1 to 3 and Comparative Examples 1 to 2 to the same height (to a height of 220 to 670 mm in a longitudinal direction of the reactors).

With regard to a reaction flow condition, a mole ratio of butene to oxygen to steam to nitrogen was 1:1:5:4. GHSV of butene was 450 h$^{-1}$BE, and oxidative dehydrogenation was carried out at a reaction temperature of 340° C. A 2-butene mixture including trans-2-butene and cis-2-butene mixed in a ratio of 6:4 was used as the butene, and reaction was allowed to proceed.

In the case of Comparative Example 1, runaway reaction was caused by excess heat during reaction, and thus, reaction was stopped during supply of butene.

[Property Evaluation]

Hot Spot (Maximum Exothermic Peak Temperature, ° C.): A thermocouple was installed in a gas flow direction in a reactor, and a maximum exothermic peak (° C.) was measured at intervals of 5 mm from an inlet to an outlet of the reactor. Results are shown in Table 1 and FIG. 3.

Td (Temperature Change at Position Before 50 mm in Longitudinal Direction of Reactor Based on Hot Spot (° C.)): With regard to FIG. 3 illustrating the measured hot spot results, temperature change (° C.) at a position before 50 mm in a longitudinal direction of the reactor based on a hot spot in the reactor was observed. Results are summarized in a Td column of Table 1.

COx Selectivity (% by Weight): Reaction products were analyzed by means of a gel chromatography-thermal conductivity detector (GC with TCD detector), and CO and $CO_2$ contents are summarized in Table 1.

TABLE 1

| Classification | Weight ratio of catalyst to inert binder | Hot spot (° C.) | Td | COx selectivity (% by weight) |
| --- | --- | --- | --- | --- |
| Example 1 | 17:83 | 439 | 52 | 14.12 |
| Example 2 | 5:95 | 398 | 6 | 19.15 |
| Example 3 | 3:97 | 391 | 5 | 21.24 |
| Comparative Example 2 | 4.2:95.8 (physical mix ratio) | 501 | 97 | 16.21 |

As shown in Table 1 and FIG. 3, it was confirmed that, in the cases of Examples 1 to 3 of the present invention, a hot spot temperature was relatively low and COx selectivity was partially improved, compared to Comparative Example 2 in which a physically dispersed product was provided. In addition, it was confirmed that, in the cases of Examples 1 to 3 of the present invention, Td was 52 which was lower than 97 of Comparative Example 2.

Meanwhile, it was confirmed that, considering the case of Comparative Example 1 in which a catalyst and an inert binder were mixed in a ratio of 100 to 0 and, accordingly, reaction was stopped during supply of butene due to runaway reaction caused by excess heat during reaction, heat generation control effect according to the present invention was considerable.

[Additional Property Evaluation]

Conversion Rate (%): Calculated according to Mathematical Equation 1 below based on data analyzed by gas chromatography after butadiene generation reaction. Results are summarized in Table 2 below.

Conversion rate (%)=(moles of reacted 2-butene/ moles of added 2-butene)×100 [Mathematical Equation 1]

Selectivity (%): Calculated according to Mathematical Equation 2 below based on data analyzed by gas chromatography. Results are summarized in Table 2 below.

Selectivity (%)=(moles of generated 1,3-butadiene/ moles of reacted 2-butene)×100 [Mathematical Equation 2]

Yield (%): Calculated according to Mathematical Equation 3 below based on data analyzed by gas chromatography. Results are summarized in Table 2 below.

Yield (%)=(moles of collected 1,3-butadiene−moles of added 2-butene/moles of added 1-butene)× 100 [Mathematical Equation 3]

TABLE 2

| Classification | Weight ratio of catalyst to inert binder | Conversion rate (%) | Selectivity (%) | Yield (%) | Hot spot (° C.) | COx selectivity (% by weight) |
| --- | --- | --- | --- | --- | --- | --- |
| Example 1 | 17:83 | 83.75 | 83.36 | 69.81 | 439 | 14.12 |
| Example 2 | 5:95 | 53.71 | 77.93 | 41.86 | 398 | 19.15 |
| Example 3 | 3:97 | 31.65 | 69.22 | 21.91 | 391 | 21.24 |
| Comparative Example 2 | 4.2:95.8 (physical mix ratio) | 81.39 | 82.11 | 66.83 | 501 | 16.21 |

As shown in Table 2, it was confirmed that Example 1 according to the present invention maintained a conversion rate, selectivity, and yield of Comparative Example 2. That is, it can be confirmed that, when the hot spot and COx selectivity results summarized in the above Table 1 are considered, the present invention may effectively produce butadiene while preventing catalyst damage or side reaction by controlling excess heat generation and lowering COx selectivity.

Additionally, it can be confirmed that, examining Examples 2 and 3, catalyst mix ratios of which are different from that of Example 1, Examples 2 and 3 exhibit a low conversion rate which is considered to be caused because active sites of the catalyst are less exposed from a pellet surface. From this result, it can be confirmed that, to provide performance similar to that of the physically mixed catalyst of Comparative Example 2, a catalyst should be molded in a higher content than those used in Examples 2 and 3.

DESCRIPTION OF SYMBOLS a1, b1: Ferrite-based catalyst a2, b2: Inert binder

The invention claimed is:

1. A ferrite-based catalyst composite, comprising 20 to 99% by weight of inert binder particles and 1 to 80% by weight of ferrite-based catalyst granules dispersed and inserted into the inert binder particles.

2. The ferrite-based catalyst composite according to claim 1, wherein the ferrite-based catalyst granules are derived from an oxide of a trivalent iron and a divalent metal, wherein the divalent metal is at least one ferrite catalyst selected from the group consisting of zinc (Zn), magnesium (Mg), manganese (Mn), and cobalt (Co).

3. The ferrite-based catalyst composite according to claim 1, wherein an average particle diameter of the ferrite-based catalyst granules is 0.1 to 1.25 mm.

4. The ferrite-based catalyst composite according to claim 1, wherein the inert binder is one or more selected from the group consisting of an aluminum compound, a silica compound, and a silica aluminum compound.

5. The ferrite-based catalyst composite according to claim 1, wherein the catalyst composite has a spherical shape having a diameter of 1 to 20 mm and a circular or irregular cross section; a cylindrical shape having a diameter of 1 to 20 mm, a circular or irregular cross section, and a height of 1 to 20 mm; or a prism having a diameter of 1 to 20 mm, a cross section of a square or irregular cross section, and a height of 1 to 20 mm.

6. A method of preparing butadiene, wherein a reactor is filled with the ferrite-based catalyst composite according to claim 1, butadiene is prepared from C4 raffinate, and, when a change in hot spot temperature (° C.) at a position before 50 mm in a longitudinal direction of the reactor is Td based on a hot spot inside the reactor in which a layer composed of the catalyst composite is formed, $Td \leq 65$.

* * * * *